(12) United States Patent
Yuki et al.

(10) Patent No.: US 9,738,730 B2
(45) Date of Patent: Aug. 22, 2017

(54) POLYSACCHARIDE POWDER AND ANTI-ADHESIVE MATERIAL CONTAINING THE SAME

(71) Applicant: TERUMO KABUSHIKI KAISHA, Shibuya-ku, Tokyo (JP)

(72) Inventors: Risa Yuki, Kanagawa (JP); Taishi Niimi, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/769,397

(22) PCT Filed: Feb. 13, 2014

(86) PCT No.: PCT/JP2014/053378
§ 371 (c)(1),
(2) Date: Aug. 20, 2015

(87) PCT Pub. No.: WO2014/129382
PCT Pub. Date: Aug. 28, 2014

(65) Prior Publication Data
US 2016/0002362 A1    Jan. 7, 2016

(30) Foreign Application Priority Data
Feb. 25, 2013  (JP) .................................. 2013-034208

(51) Int. Cl.
  *C08B 37/00*   (2006.01)
  *A61K 31/718*  (2006.01)
  (Continued)

(52) U.S. Cl.
  CPC ........ *C08B 37/0009* (2013.01); *A61K 31/718* (2013.01); *A61L 31/042* (2013.01); *C08L 3/02* (2013.01); *C08L 5/00* (2013.01)

(58) Field of Classification Search
  CPC ..... C08B 37/0009; C08B 31/12; A61K 47/36; A61K 31/718; A61L 15/16; A61L 9/14
  See application file for complete search history.

(56) References Cited

U.S. PATENT DOCUMENTS 5,576,025 A * 11/1996 Akiyama ............. A61K 9/1617
                                                    424/487
5,849,233 A * 12/1998 Altieri ..................... C08B 30/12
                                                    127/32
(Continued)

FOREIGN PATENT DOCUMENTS

EP    3006056 A1   4/2016
JP    63-105004 A  5/1988
(Continued)

OTHER PUBLICATIONS

Notification Concerning Transmittal of International Preliminary Report on Patentability (Form PCT/IB/326), Notification of Transmittal of Translation of the International Preliminary Report on Patentability (Form PCT/IB/338 and PCT/IB/373) and the Written Opinion of the International Searching Authority (Form PCT/ISA/237) issued on Sep. 3, 2015, by the International Bureau of WIPO in corresponding International Application No. PCT/JP2014/053378. (21 pages).

(Continued)

*Primary Examiner* — Alexandre Ferre
(74) *Attorney, Agent, or Firm* — Buchanan Ingersoll & Rooney PC

(57) ABSTRACT

The present invention provides a means for improving water-solubility of polysaccharide. A polysaccharide powder according to the present invention has a particle size distribution in which 30 vol % or more of the total volume of the powder has particle sizes of 200 to 750 μm.

10 Claims, 1 Drawing Sheet

(51) Int. Cl.
*C08L 3/02* (2006.01)
*A61L 31/04* (2006.01)
*C08L 5/00* (2006.01)

(56) References Cited

U.S. PATENT DOCUMENTS

| | | | |
|---|---|---|---|
| 2003/0124087 A1* | 7/2003 | Kim | A61L 31/041 424/78.18 |
| 2008/0058469 A1 | 3/2008 | Abe et al. | |
| 2008/0294099 A1 | 11/2008 | Yatabe et al. | |
| 2009/0062233 A1 | 3/2009 | Ji et al. | |
| 2011/0282050 A1* | 11/2011 | Merz et al. | 536/91 |
| 2012/0164451 A1* | 6/2012 | Masue | 428/402 |
| 2014/0308365 A1 | 10/2014 | Fukuda et al. | |

FOREIGN PATENT DOCUMENTS

| JP | 01-275601 A | 11/1989 |
|---|---|---|
| JP | 1-275601 A | 11/1989 |
| JP | 2000-063565 A | 2/2000 |
| JP | 2008-289986 A | 12/2008 |
| JP | 2011-505428 A | 2/2011 |
| JP | 2011-509932 A | 3/2011 |
| JP | 2011-084588 A | 4/2011 |
| JP | 4854299 B2 | 1/2012 |
| WO | WO 2004/080502 A1 | 9/2004 |
| WO | WO 2005/087289 A1 | 9/2005 |
| WO | WO2009/070168 A1 | 6/2009 |
| WO | WO 2009/091549 A1 | 7/2009 |
| WO | WO 2011/027729 A1 | 3/2011 |
| WO | WO 2013/077414 A1 | 5/2013 |

OTHER PUBLICATIONS

International Search Report (PCT/ISA/210) mailed on Apr. 15, 2014, by the Japanese Patent Office as the International Searching Authority for International Application No. PCT/JP2014/053378.
Written Opinion (PCT/ISA/237) mailed on Apr. 15, 2014, by the Japanese Patent Office as the International Searching Authority for International Application No. PCT/JP2014/053378.
Extended Search Report issued by the European Patent Office in corresponding European Patent Application No. 14754523.0 on Sep. 28, 2016 (8 pages).

\* cited by examiner

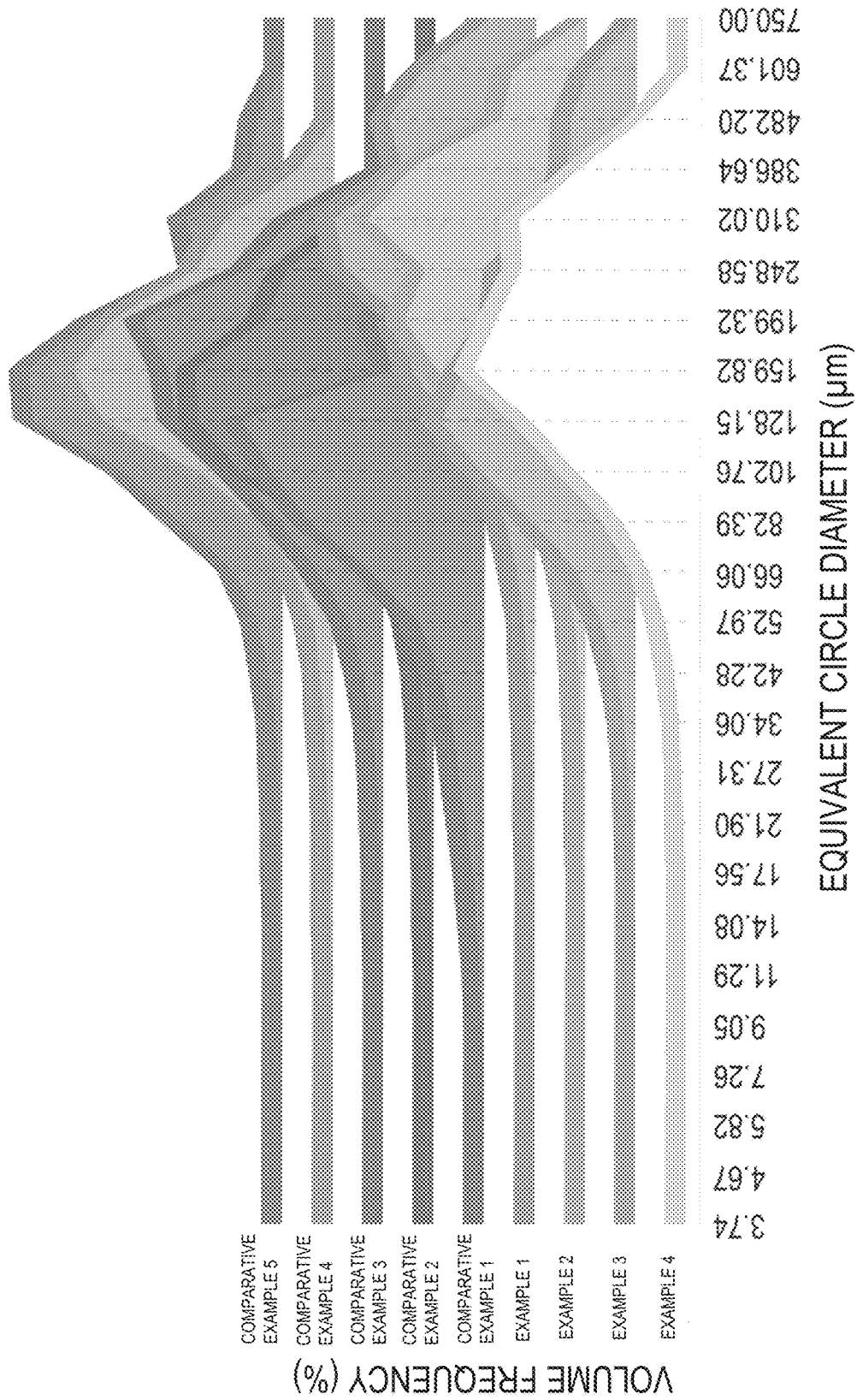

POLYSACCHARIDE POWDER AND ANTI-ADHESIVE MATERIAL CONTAINING THE SAME

TECHNICAL FIELD

The present invention relates to a polysaccharide powder and an anti-adhesive material containing the same. More particularly, the present invention relates to improvement for increasing water-solubility of polysaccharide.

BACKGROUND ART

Surgical operations in surgery may damage biological tissues. Exposure of biological tissues to the air by incisions has been known to dry or oxidize biological tissues, resulting in damaged biological tissues. The damaged tissues may cause postoperative inflammation or the like to induce the adhesion between tissues that should be naturally separated. Such postoperative adhesion between tissues may lead to, for example, serious complications, such as ileus and infertility, in an abdomen. Various types of anti-adhesive materials have thus been developed to cover damaged sites of biological tissues for the prevention of adhesion.

Currently-known anti-adhesive materials have been mainly composed of biological polymer materials, such as polysaccharides and polypeptides, which are unlikely to cause adverse effects on living bodies. Such anti-adhesive materials are in various forms, such as powder, sheet, jelly, or liquid. Of these, liquid anti-adhesive materials have particularly attracted attention because of their operability of coating formed by being sprayed to target sites of biological tissues.

Of such anti-adhesive materials, for example, an anti-adhesive material disclosed in Patent Literature 1 includes a crosslinkable polysaccharide derivative having an active ester group reactive with an active hydrogen-containing group in a polysaccharide side chain introduced therein. The crosslinkable polysaccharide derivative can, upon contact with water under alkaline conditions, form a crosslinked structure through covalent bonding between the active ester group and an active hydrogen-containing group. Patent Literature 1 has disclosed, as a preferred embodiment, a method of preventing adhesion which includes applying an aqueous solution of the above crosslinkable polysaccharide derivative to a target site of biological tissues and then spraying an aqueous solution of a pH adjuster for generating alkaline conditions onto the target site to cause gelation of the crosslinkable polysaccharide derivative.

In addition, applicators capable of simultaneously spraying two chemical solutions, including the aqueous solution of the crosslinkable polysaccharide derivative and the aqueous solution of a pH adjuster, have been developed (e.g., Patent Literature 2). The use of such applicators allows the coating of the target site with an anti-adhesive material by one-time spraying. Since polysaccharides dissolved in water are more subject to deterioration than dry solid polysaccharides, aqueous solutions of polysaccharides are desirably prepared each time in surgical practice by addition of water to dry solid polysaccharides.

CITATION LIST

Patent Literatures

Patent Literature 1: WO 2005/087289 A (corresponding to U.S. Patent Application Publication No. 2008/058469)

Patent Literature 2: JP-2008-289986 A (corresponding to U.S. Patent Application Publication No. 2008/294099)

SUMMARY OF INVENTION

Technical Problem

However, polysaccharides preferably used as the anti-adhesive material are normally poorly soluble in water since they have a hydrophobic functional group or a large molecular weight. It thus takes a long time to dissolve dry solid polysaccharides in water, which makes difficult quick preparation of an aqueous polysaccharide solution. For this, anti-adhesive materials containing poorly water-soluble polysaccharides are disadvantageously unsuitable for urgent application in surgical practice.

Therefore, the present invention has been made in light of the aforementioned circumstances and aims at providing- a means for improving water-solubility of polysaccharides.

Means for Solving Problem

The present inventors have intensively studied to solve the aforementioned problems. As a result, the present inventors have found that polysaccharide powder having a specific particle size distribution shows a significantly improved solubility (water-solubility), to complete the present invention.

In other words, the aforementioned problem of the present invention can be solved by a polysaccharide-containing powder having a particle size distribution in which 30 vol % or more of the total volume of the powder has a particle size of 200 to 750

BRIEF DESCRIPTION OF DRAWINGS

FIG. 1 is a graph showing a volume frequency distribution (dynamic image analysis) of the polysaccharide powders (1) to (4) and the comparative polysaccharide powders (1) to (5) obtained in Examples 1 to 4 and Comparative Examples 1 to 4.

DESCRIPTION OF EMBODIMENTS

The present invention provides a polysaccharide-containing powder (herein also referred to as "polysaccharide powder of the present invention" or "polysaccharide powder") having a particle size distribution in which 30 vol % or more of the total volume of the powder has a particle size (diameter) of 200 to 750 μm. The above constitution can improve water-solubility of polysaccharide. The polysaccharide powder of the present invention may consist of only polysaccharide(s), or may include polysaccharide(s) and a component than other the polysaccharide(s).

A polysaccharide solution (particularly an aqueous polysaccharide solution) has been conventionally used as an anti-adhesive material because of their operability of easily covering a target site of biological tissue by the spraying of the polysaccharide solution. Polysaccharide, however, is typically poorly soluble in water since they have a hydrophobic functional group or a large molecular weight. Urgent application of the polysaccharide solution in surgical practice thus requires an improvement in water-solubility of polysaccharide powder. An ordinal method of obtaining a polysaccharide powder involves loading a polysaccharide solution into a vial and freeze-drying the solution. Since it takes a long time (e.g., about 5 minutes) to completely dissolve the freeze-dried polysaccharide powder obtained by the above method at high concentration, the freeze-dried polysaccharide powder cannot meet urgent application particularly in medical practice. Therefore, there is a need for improving water-solubility of polysaccharide powder (a rate of dissolution in water).

To solve the low solubility of such freeze-dried polysaccharide powder, for example, a method of producing freeze-dried polysaccharide powder has been proposed which comprises freeze-drying a polysaccharide solution in a sheet form on a tray and pulverizing the freeze-dried product to increase a specific surface area (contact area with water) to improve the solubility. The experiments on the method described above by the present inventors have indicated that a time for complete dissolution of the freeze-dried polysaccharide powder can be reduced to some extent (e.g., about 2 minutes), which has showed some improvements in water-solubility. However, only simple powderization has formed aggregates of the powder during dissolution or has caused adhesion of the powder to the bottom of the vial, which imposes a high risk of low solubility and thus failed to provide a sufficient improvement.

A method of improving water-solubility has also been proposed which comprises forming a freeze-dried polysaccharide powder having a porous structure and adjusting a size and distribution of pores in a specific range (WO 2011/027706 (corresponding to U.S. Patent Application Publication No. 2012/157672)). However, the method requires accurate adjustment of freeze-drying conditions, and a simpler method of producing a polysaccharide powder excellent in water-solubility has been desired.

The present invention has a feature in that polysaccharide powder has a specific particle size distribution in which 30 vol % or more of the total volume of the powder has a particle size (diameter) of 200 to 750 μm. The water-solubility can be improved by adjusting a particle size so that a large volume of powder is large. The water-solubility can be further improved by adjusting a wide range of particle sizes (a wide particle size distribution). Therefore, an aqueous polysaccharide solution can be prepared quickly in surgical practices and in various medical practices such as preparation of injections and infusion solutions.

Although the mechanism by which the polysaccharide powder according to the present invention exhibits good water-solubility is unclear, it is presumed as follows. It should be noted that the present invention is not limited by the following. Specifically, comminution (reduction in particle size) of polysaccharide powder is normally preferred in terms of rapid dissolution in water. Since van der Waals force, which acts between particles (powder), is inversely proportional to the square of the particle size, a larger van der Waals force acts between particles (powder) with smaller particle sizes. An electrostatic force acts between particles (powder) under low-humidity (dry) conditions, whereas a liquid crosslinking force acts between particles (powder) under moderate-humidity (e.g., RH 60% or more) conditions to cause aggregation of the particles. For this, the presence of only fine powder did not always provide good water-solubility (uniform solubility) because the van der Waals force, electrostatic force, liquid crosslinking force, or the like induce binding of fine powder particles, formation of aggregates of fine powder during dissolution, or adhesion of fine powder to a surface of container (e.g. a bottom side of container). The present inventors have made intensive studies on the above phenomenon, to find that polysaccharide powder including certain percentages (30 vol % or more) of polysaccharide powder with particle sizes of 200 to 750 μm contributes to an improvement in solubility. Regarding the polysaccharide powder including a large volume of powder with such sizes, weak van der Waals force and electrostatic force act between powder particles due to the size of the powder, and liquid crosslinking thus hardly occurs, which reduces or eliminates the binding between powder particles. Even if the polysaccharide powder includes fine powder with smaller sizes than the above particle sizes, the powder with particle sizes of 200 to 750 μm is present between fine powder particles, which inhibits or prevents the above phenomenon to reduce or eliminate the binding between fine powder particles, the formation of aggregates during dissolution, and the adhesion to a surface of container. Therefore, the polysaccharide powder of the present invention can exhibit good water-solubility (rapid dissolution in water). Therefore, an anti-adhesive material containing the polysaccharide powder of the present invention can be quickly used in urgent application in surgical practices and in various medical practices such as preparation of injections and infusion solutions. The above advantageous effects can be effectively exerted particularly when the polysaccharide has a hydrophobic group.

The embodiments of the invention will be described below.

As used herein, the expression "X to Y" indicating a range means "X or more and Y or less", and the terms "weight" and "mass", "wt %" and "wt % ", and "parts by weight" and "parts by mass" are considered interchangeably. Unless otherwise specified, the operations and the determination of physical properties or the like are carried out under the conditions of room temperature (20° C. to 25° C.)/relative humidity of 40% to 50%.

[Polysaccharide Powder]

The polysaccharide powder of the present invention has a particle size distribution in which 30 vol % or more of the total volume of the powder has particle sizes (diameters) of 200 to 750 μm. The polysaccharide powder having such a particle size distribution exhibits good water-solubility. When polysaccharide powder having a particle size distribution of 200 to 750 μm accounts for less than 30 vol % of the total volume, the polysaccharide powder is poorly soluble in water and thus unsuitable for emergency surgical practice. The polysaccharide powder of the present invention preferably has a particle size distribution in which the particle size of 40 vol % or more, more preferably 50 vol % or more, still more preferably 60 vol % or more of the total volume is 200 to 750 μm. The upper limit of the content of the polysaccharide powder having a particle size distribution of 200 to 750 μm is not particularly limited, but is preferably 70 vol % or less, more preferably 65 vol % or less, still more preferably 55 vol % or less in terms of improvedwater-solubility .

As used herein, the expression "exhibiting good water-solubility" means that a minimum dissolution time is 90 seconds or less in the "Evaluation on Solubility" in the following Examples. The minimum dissolution time when measured in the "Evaluation on Solubility" in the following Examples is preferably 60 seconds or less, more preferably 30 seconds or less. The lower limit of the minimum dissolution time is not particularly limited since a shorter dissolution time is preferred. The minimum dissolution Lime of at least 1 second is normally sufficient in light of the application in surgical practice. The number of samples for which the minimum dissolution time is 30 seconds or less is preferably the largest in the "Evaluation on Solubility" in the following Examples; the minimum dissolution time for 60% or more of samples among all samples is more preferably 30 seconds or less; and the minimum dissolution time for 70% or more of samples among all samples is still more preferably 30 seconds or less.

As used herein, the term "polysaccharide" refers to a polymer formed by bonding monosaccharides through glycosidic linkages and having a molecular weight of 1,000 or more.

As used herein, the "content (particle size distribution) of polysaccharide powder having a particle size distribution in which the particle size is 200 to 750 μm" is expressed as a percentage (vol %) obtained by computing an equivalent circle diameter (particle size equivalent to a project area) from a project area by conversion of images of 10,000 particles using dynamic image analysis (measuring device: available from Seishin Enterprise Co., Ltd., trade name: PITA-2); calculating a volume frequency distribution (volume distribution (on a number basis) based on the total volume (the number×the volume of particles); and calculating a percentage (vol %) of the volume of the polysaccharide powder having particle sizes (diameters) of 200 to 750 μm by dividing the volume by the total volume.

A peak top of the polysaccharide powder of the present invention is not particularly limited, but is preferably from 100 to 500 μm, more preferably 120 to 350 μm, still more preferably 120 to 320 μm. The polysaccharide powder having such a peak top is particularly efficiently present between fine powder particles with small particle sizes, which can inhibit or prevent the bonding between fine powder particles, the formation of aggregates during dissolution, and the adhesion to a surface of container. As used herein, the expression "peak top of polysaccharide powder" refers to a particle size (diameter) (μm) at the highest point (peak) (particle size with the highest frequency) of volume distribution (on the basis of the number) measured as above.

A particle size distribution of the polysaccharide powder of the present invention is not particularly limited, but the polysaccharide powder preferably has a wide particle size distribution. Specifically, the particle size at 10% of cumulative volume (D10) of the polysaccharide powder is preferably 60 to 120 μm, more preferably 65 to 110 μm. The particle size at 90% of cumulative volume (D90) of the polysaccharide powder is preferably 300 to 520 μm, more preferably 320 to 515 μm. Furthermore, the particle size at 50% of cumulative volume (D50) of the polysaccharide powder is preferably more than 120 μm and less than 300 μm, more preferably 130 to 270 μm. When the polysaccharide powder has such a wide particle size distribution, powder particles with larger particle sizes are more effectively present between fine powder particles with smaller particle sizes, which can efficiently inhibit or prevent the bonding between fine powder particles, the formation of aggregates during dissolution, and the adhesion to a surface of container.

Examples of monosaccharides constituting the polysaccharide powder of the present invention include, but are not limited to, ribose, xylose, arabinose, glucose, mannose, galactose, fructose, sorbose, rhamnose, fucose, and ribodeose, and monosaccharide derivatives containing an optional functional group. Polysaccharide may be composed of only one of these monosaccharides or maybe composed of a combination of two or more monosaccharides, and may be linear or branched. Naturally-occurring polysaccharide(s) may be used or synthetic polysaccharide(s) may be used.

A polysaccharide which constitutes a main chain of the polysaccharide may be any polysaccharide having two or more units of the above monosaccharide structures in its main backbone. Examples thereof include polysaccharides formed by the covalent bonding of disaccharides, such as trehalose, sucrose, maltose, cellobiose, gentiobiose, lactose, and melibiose; polysaccharides including trisaccharides or higher saccharides, such as raffinose, gentianose, melezitose, stachyose, dextrin, dextran, and cellulose; and derivatives of such polysaccharides further containing a functional group. Such polysaccharides maybe naturally occurring or may be artificially synthesized. Of these polysaccharides, polysaccharides containing glucose or glucose derivatives are preferred in terms of the achievement of biological administration. Specifically, at least one polysaccharide selected from the group consisting of dextrin, dextran, cellulose, and derivatives thereof is more preferably contained.

Dextran is used as a plasma substitute and available under the trade name "Dextran T fractions" (Amersham Biosciences K.K.).

Dextrin is a hydrolysate of starch and is a mixture of glucose polymers having different molecular chain lengths. The glucose units in dextrin contain mainly α-1,4 bonds, and normally a certain degree of α-1,6 bonds. In the present invention, a type of starch for producing dextrin is not particularly limited, and therefore an abundance of α-1,6 bonds is not particularly limited, either. The dextrin used in the present invention typically has a molecular weight (Mw) of about 10 to 200 kDa in consideration of availability, physical properties at the time of use, handling ability, and film formation properties. In the present invention, any commercially available polysaccharide can be used for the polysaccharides. Polysaccharides that have been already used in medical applications can be suitably used from a safety viewpoint in the present invention. in particular, dextrin is particularly suitable polysaccharide because of no reports on anaphylactic shock associated with dextrin, conventional usage of dextrin in peritoneal dialysis, and no reports on problems with biological compatibility.

The polysaccharides according to this embodiment preferably contains at least one selected from the group consisting of a carboxyl group, an active ester group, a carboxylate salt, an amino group, and an aldehyde group. Since such a functional group can serve as a crosslinking point to form an ester bond or amide bond, polysaccharides having such a functional group are suitable as a component of an anti-adhesive material. When an anti-adhesive material includes such a functional group(s), the above functional group (s) and hydroxy group (s) in the polysaccharide, hydroxy group on a surfaces of biological tissue, and the like form an ester bond or amide bond to cause cross linking in an aqueous solution containing the polysaccharides under alkaline conditions. This causes gelation of polysaccharide powder (anti-adhesive material) to cover a surface of biological tissue.

Examples of the polysaccharide having a carboxyl group include polysaccharides having a carboxyalkyl group introduced into the hydroxy group. Suitable carboxyalkyl group includes carboxyalkyl groups having 2 to 5 carbon atoms, specifically, a carboxymethyl group, a carboxyethyl group, a carboxypropyl group, a carboxy isopropyl group, and a carboxybutyl group. Of these, a carboxymethyl group or a carboxyethyl group is preferred, and a carboxymethyl group (carboxymethylated polysaccharides) is more preferred. In the present invention, the carboxy group in the polysaccharides is desirably "non-salt type" without coordinated salts. The active esterified polysaccharide finally obtained is desirably in a non-salt form. As used herein, the term "salt" encompasses inorganic salts of, for example, alkali metals and alkaline earth metals; quaternary amines, such as tetrabutylammonium (TBA); and haloid salts, such as chloromethylpyridinium iodide. The term "non-salt type" means that the "salt" is not coordinated, and the term "non-salt form" means that the salt is not contained.

The carboxylation reaction of polysaccharide can be carried out using known oxidation reactions without limitation. When a hydroxyl group of polysaccharide is oxidized to form carboxylic acid, the reaction is not limited to particular types, but examples include dinitrogen tetroxide oxidation, fuming sulfuric acid oxidation, phosphoric acid oxidation, nitric acid oxidation, and hydrogen peroxide oxidation. Each oxidation can be performed by selecting a commonly known reaction using a reagent(s). The reaction conditions can be appropriately set depending on the amount of carboxy group introduced. For example, acidic polysaccharide having carboxylic acid can be prepared by suspending a polysaccharide as a material in chloroform or carbon tetrachloride and adding dinitrogen tetroxide thereto to oxidize a hydroxyl group of polysaccharide.

A known method can be used for the carboxyalkylation reaction of the polysaccharide without limitation. Specifically, for the carboxymethylation reaction, the reaction using monochloroacetic acid after alkalization of the polysaccharide can be selected. The reaction conditions can be appropriately set depending on an amount of carboxymethyl group introduced. The polysaccharide here is typically subjected to the reaction in the form of an aqueous solution. Acidic polysaccharide containing a carboxy group is generally precipitated using a poor solvent (typically alcohol) and dried under reduced pressure.

A method of introducing a carboxy group into polysaccharide can be either carboxylation or carboxyalkylation, without limitation.

The carboxyalkylation, particularly carboxymethylation is preferred since the decrease in molecular weight of the polysaccharide due to the carboxy group introduction reaction is small and the amount of carboxy group introduced is relatively easy to control. The carboxymethyl group is also referred below to as "CM-."

Next, examples of polysaccharide having an active ester group (active esterified polysaccharide) include ones formed by esterification between the carboxyl group in polysaccharide having carboxyl group and N-hydroxy amine compound.

The active ester group is formed by the reaction of polysaccharide with an electrophilic group introducing agent. In this case, the polysaccharide may be used alone or in a mixed form. The active ester group is a group in which a carbonyl carbon of a carboxy group is bound to an electrophilic group stronger than common alcohol, and the ester bond dissociates in water in the presence of an alkali. As the electrophilic group introducing agent for forming such an active ester group, a relatively inexpensively available N-hydroxyamine compound is typically used. Specific typical examples include N-hydroxysuccinimide, N-hydroxynorbornene-2,3-dicarboxyimide, ethyl 2-hydroxyimino-2-cyanoacetate, 2-hydroxyimino-2-cyanoacetic acid amide, N-hydroxypiperidine, N-hydroxyphthalimide, N-hydroxyimidazole, and N-hydroxymaleimide. These compounds may be used alone or in mixture. Of these compounds, N-hydroxyimide, particularly N-hydroxysuccinimide (NHS) is preferred because it has been used in the field of peptide synthesis and easily commercially available.

The polysaccharide used for active esterification contains a carboxy group (regarded as one molecule) in an amount of typically 0.1 to 5 mmol/g, preferably 0.4 to 3 mmol/g, more preferably 0.5 to 2 mmol/g per gram of dry mass of the polysaccharide. The amount of the carboxy group of less than 0.1 mmol/g would often result in an insufficient number of active ester groups that are derived from the carboxy group and serve as crosslinking points. In contrast, the amount of the carboxy group of more than 5 mmol/g may make it difficult Lo dissolve active esterified polysaccharide (uncrosslinked) in a solvent including water. The amount of carboxy group of polysaccharide can be quantified with acid-base back titration using phenolphthalein as an indicator (see the section of "Method of Measuring Amount of Carboxy Group in Polysaccharide" in the following Examples. The carboxy group that is not converted into active ester group may remain in the final active esterified polysaccharide. Therefore, the amount of carboxy group as described above is a sum of active ester group in the final active esterified polysaccharide and carboxy group that is not converted into active ester group.

The polysaccharide is normally subjected to the esterification reaction as a solution in an aprotic polar solvent. An aprotic polar solvent is a polar solvent having no proton capable of forming a hydrogen bond with a nucleophilic agent having an electrically positive functional group. Examples of the aprotic polar solvent include, but are not limited to, dimethyl sulfoxide (DMSO), N,N-dimethylformamide, N-methyl-2-pyrrolidone, N,N-dimethylacetamide, and 1,3-dimethyl-2-imidazolidinone. DMSO can be suitably used as a solvent because of good solubility of polysaccharide in the solvent. The suitable "non-salt type" of acidic polysaccharide can be normally dissolved in the above solvents at about 20° C. to 120° C. (by heating as desired).

The esterification reaction between a polysaccharide and an electrophilic group introducing agent is typically carried out in the presence of a dehydration condensation agent. The dehydration condensation agent withdraws one water molecule produced by condensation between the carboxy group and the electrophilic group introducing agent, in other words, dehydrates the polysaccharide to form an ester linkage between them. Examples of the dehydration condensation agent include, but are not limited to, 1-ethyl-3-dimethylaminopropylcarbodiimide hydrochloride (EDC) and 1-cyclohexyl- (2-morpholinyl-4-ethyl) -carbodiimidemeso-p-toluene sulfonate. Of these, 1-ethyl-3-dimethylaminopropylcarbodiimide hydrochloride (EDC) is preferred because it has been already used in the field of peptide synthesis and easily commercially available.

The reaction temperature in the esterification reaction process is not particularly limited, but is preferably 0° C. to 70° C., more preferably 20° C. to 40° C. The reaction time, which can vary with reaction temperature, is typically 1 to 48 hours, preferably 12 to 24 hours.

The active esterified polysaccharide produced by the esterification reaction may be recovered by crystallization, or the active esterified polysaccharide may be brought into contact with polyvalent carboxylic acid before precipitation. The polyvalent carboxylic acid here may be a di- or higher carboxylic acid and normally selected from easily available dicarboxylic acids and tricarboxylic acids. in particular, succinic acid and malic acid are preferred as a dicarboxylic acid and citric acid is preferred as a tricarboxylic acid because they have been conventionally used as pharmaceutical additives. These carboxylic acids may be used in combination. The amount of polyvalent carboxylic acid used is typically one equivalent or more, typically 1 to 10 equivalents in terms of the acid equivalent per mole of an added electrophilic group introducing agent. The polyvalent carboxylic acid in this range can finally provide a dry product of active esterified polysaccharide that does not generate any insoluble material in water. It is preferably 1.5 equivalents or more. An excess amount of the polyvalent carboxylic acid would tend to result in a high change rate of the average molecular weight Mw over time during drying. It is thus preferably 9 equivalents or less, more preferably 7.5 equivalents or less. It is typically 3 equivalents. The contact between the active esterified polysaccharide and the polyvalent carboxylic acid is achieved by, specifically, adding the polyvalent carboxylic acid to a reaction solution obtained after the esterification reaction and mixing the reaction solution. The mixing time is not particularly limited, but is typically 1 to 60 minutes.

After the contact described above, the active esterified polysaccharide is precipitated in a conventional manner and recovered. In general, the reaction solution is added to an excess amount of a poor solvent, such as alcohols and acetone, whereby the active esterified polysaccharide is precipitated. The active esterified polysaccharide is then recovered by an appropriate method, such as decantation, centrifugation, and filtration. The precipitate is preferably washed with a poor solvent at least once for purification. The filtration and/or washing means or the like in this precipitation/purification process can remove the polyvalent carboxylic acid added to the reaction system as well as an unreacted electrophilic group introducing agent, a dehydration condensation agent, and by-products of the reaction, so that substantially no polyvalent carboxylic acid is present in the final active esterified polysaccharide.

Since the active esterified polysaccharide is unstable in water, the active esterified polysaccharide obtained after the precipitation/purification process is typically dried under reduced pressure. The drying under reduced pressure is desirably performed at a temperature of 45° C. or less typically for at least one hour, preferably 4 hours, normally about 24 hours. The active esterified polysaccharide obtained according to the production process of the present invention shows an inhibited increase in molecular weight over time during drying under reduced pressure.

Polysaccharide having a carboxylate is formed by conically bonding a cation other than a hydrogen ion with a carboxylate ion left after removal of hydrogen ion from the carboxyl group present in polysaccharide having a carboxyl group. Examples of the cation include alkali metal ions, alkaline earth metal ions, and quaternary ammonium ions, such as tetra(n-butyl)ammonium and tetra (n-propylmethyl) ammonium ions.

Examples of polysaccharide having an amino group include polysaccharides containing glucosamine and amino sugar such as glucosamine and polysaccharides containing an isourea intermediate (polysaccharides containing the structure of the following chemical formula 1).

[Chemical Formula 1]

[Formula 1]

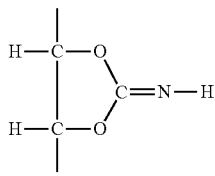

Examples of polysaccharide having an aldehyde group include polysaccharides containing aldoses in the reducing terminal of the polysaccharides.

Polysaccharide having such a functional group may be naturally occurring ones, or may be produced according to chemical or biological techniques. To produce polysaccharide having the functional group, a conventionally known means can be appropriately employed.

It should be noted that the polysaccharide powder of the present invention may contain a component other than the polysaccharide. Examples of the component other than the polysaccharide include, but are not limited to, oligosaccharides having a molecular weight of less than 1,000.

The weight-average molecular weight (Mw) of the polysaccharide is not particularly limited, but is preferably 20,000 to 200,000, more preferably 30,000 to 120,000. The polysaccharide powder with such a relatively large molecular weight even exhibits good water-solubility as long as it has the particle size distribution according to the present invention. The use of the polysaccharide powder with such a molecular weight as an anti-adhesive material allows a crosslinked polysaccharide to have good gel hardness. The weight-average molecular weight used herein is the value obtained by GPC (standard: pullulan) under the following measurement conditions.

[Formula 2]
<Measurement Conditions for Weight-Average Molecular Weight (Mw)>

Reagents: RO water, sodium nitrate

Preparation of eluent: 8.49 g of sodium nitrate is weighed out and diluted with RO water up to 2 L to give a 50 mM aqueous solution of sodium nitrate.

Preparation of sample solution: 10 mg of a sample is weighed out and diluted with 10 mL of the eluent. The solution is mixed by inversion 10 times and allowed to stand for 2 hours. The resulting solution is passed through a membrane filter to a measurement vial.

HPLC Measurement Conditions:
Measuring Device: EcoSEC HPLC-8320GPC available from Tosoh Corporation
Column: Shodex φ 8.0×300 mm, two columns
Eluent: 50 mM aqueous solution of sodium nitrate
Flow rate: 1.0 mL/min
Column temperature: 40° C.
Detector: RI
Injection volume: 100 μL A method of producing the polysaccharide of the present invention is not limited to particular methods, and known methods, including the methods disclosed in WO 2005/087289 A, JP-2011-68827 A, and JP-2008-29824 A, can be employed with or without appropriate modifications.

[Method of Producing Polysaccharide Powder]

A method of producing the polysaccharide powder of the present invention (a method of controlling the particle size distribution) may be any method that can control the particle size distribution of the polysaccharide powder so that the powder having particle sizes of 200 to 750 μm accounts for 30 vol % or more of the total volume. The particle size maybe controlled by an ordinary size classification. A method suitably employed preferably includes: preparing a polysaccharide solution by dissolving the polysaccharide prepared as described above in a solvent (polysaccharide solution-preparation step); freeze-drying the polysaccharide solution to give a freeze-dried material (freeze-drying step); and further grinding the freeze-dried material at a spin speed of 6,000 to 12,000 rpm (grinding step). That is, the present invention also provides a method of producing a polysaccharide dry powder, including: preparing a polysaccharide solution by dissolving a polysaccharide in a solvent; and freeze-drying the polysaccharide solution to give a freeze-dried material; and further grinding the freeze-dried material at a spin speed of 6,000 to 8,000 rpm. Such a method can efficiently produce the polysaccharide powder of the present invention having a particle size distribution in which 30 vol % or more of the total volume of the powder has a particle size of 200 to 750 μm.

A preferred embodiment of the method of producing the polysaccharide powder according to the present invention (the method of controlling the particle size distribution) will be described below in detail. The present invention is not limited to the following embodiment.

(Polysaccharide Solution-Preparation Step)

In this step, a polysaccharide solution is prepared by dissolving the polysaccharide prepared as described above in a solvent.

The solvent may be any solvent that can dissolve the polysaccharide. Specifically, water is preferred, and RO water (water produced by removal of impurities through a reverse osmosis membrane), distilled water, and distilled water for injection are more preferred in terms of a few impurities. The amount of the solvent is preferably, but not necessarily, 6 to 20 g, more preferably 8 to 15 g per gram of the polysaccharide.

The polysaccharide solution may also contain a stabilizer in order to stabilize the polysaccharide during the next, step (freeze-drying step). Any known stabilizer can be used as a stabilizer, without limitation. Specific stabilizers include non-reducing sugars, such as sucrose, trehalose, stachyose, and raffinose; polysaccharides, such as dextran, soluble starches, dextrin, and inulin; monosaccharides, such as apiose, arabinose, lixose, ribose, xylose, digitoxose, fucose, quercitol, quinovose, thamnose, allose, altrose, fructose, galactose, glucose, gulose, hamamelose, idose, mannose, and tagatose; disaccharides, such as primeverose, vicianose, rutinose, scillabiose, cellobiose, gentiobiose, lactose, lactulose, maltose, melibiose, sophorose, and ranose; tocopherol, tocopherol derivatives, and mannitol. The amount of the stabilizer when the polysaccharide solution contains the stabilizer is not particularly limited, but is preferably 0.5 to 1.25 g, more preferably 0.75 to 1 g, per gram of the polysaccharide, in view of the stability of the polysaccharide during the next step (freeze-drying step).

A method of dissolving the polysaccharide in the solvent is not limited to particular methods and normally performed by stirring, and may involve heating unless it has a significant adverse effect on the chemical properties of the polysaccharide. Preferably, the polysaccharide and optionally the stabilizer may be added to the solvent and then dissolved by stirring at 0 to 10° C. for 50 minutes to 1 hour. Alternatively, the stabilizer maybe added to and dissolved in the solvent in advance, and the polysaccharide may be further added and dissolved by stirring at 0 to 10° C. for 50 minutes to 1 hour. After the dissolution, the solution may be filtered (e.g., filtering) as desired in order to remove impurities.

(Freeze-drying Step)

In this step, the resulting polysaccharide solution is freeze-dried to give a freeze-dried material.

The freeze-drying conditions for the polysaccharide solution maybe any conditions that can provide the polysaccharide in proper dry state, and may be the same conditions as known in the art. For example, the freezing step involves formation of ice crystals of the polysaccharide solution. The cooling conditions for the polysaccharide solution in the freezing step may depend on the volume of the polysaccharide solution and the characteristics of a cooling device. The cooling temperature is generally, but not necessarily, decreased gradually from 0° C. to 10° C. to −30° C. to −50° C. over time for about 30 to 165minutes. When a predetermined temperature of −30° C. to −50° C. is reached, this temperature is maintained for 400 to 500 minutes. The cooling step may be performed continuously or step wisely. A cooling/freezing device used for cooling is not limited to particular devices, but preferably a cooling/freezing device that can control the cooling and freezing temperatures in order to accomplish the above freezing step, more preferably one that can control the cooling and freezing temperatures and the cooling and freezing times by a program. To facilitate the freezing step and the subsequent drying step, using a freeze dryer is particularly preferred.

After the freezing step, water in ice crystals is removed by sublimation under reduced pressure in the drying step. The condition of reduced pressure here is not particularly limited, but is typically 0.5 to 5 Pa. To achieve sublimation without converting water in ice crystals into liquid, the ice crystals are preferably maintained at 30° C. or less, for example, about −60° C. to 30° C. The drying step may be performed in one step, or may be performed in multiple steps with varying conditions. The dryer may be any dryer capable of drying under reduced pressure with cooling, and known devices can be appropriately used.

(Grinding Step)

In this step, the freeze-dried material obtained above is ground at a spin speed of 6,000 to 12,000 rpm. The resulting freeze-dried material is thus ground by impacts to yield polysaccharide powder having the particle size distribution according to the present invention. The freeze-dried material is preferably ground at a spin speed of 6,000 to 8,000 rpm. A mill that may be used here may be any device capable of grinding at the above spin speed. Examples include ultra centrifugal mills, cutter mills, hammer mills, flash mills, jet mills, ball mills, and vibration ball mills.

The grinding conditions maybe any conditions that provide the polysaccharide powder having the particle size distribution according to the present invention. Specifically, the grinding temperature is 20° C. to 30° C., more preferably about room temperature (25° C.). The grinding time is 5 to 60 minutes, more preferably 10 to 30 minutes.

In the grinding step and/or after the grinding step, additional grinding may be performed using a screen having a mesh size (diameter) of 1 to 10 mm. While or after the freeze-dried material is accordingly ground by impact (primary grinding), the material is further ground by shear force and then passed through a screen having a mesh size in a specific range (secondary grinding). This can more effectively provide the polysaccharide powder having the particle size distribution according to the present invention. In light of the particle size distribution of the polysaccharide powder of the present invention, the mesh size (diameter) of the screen is preferably 6 to 10 mm, more preferably 8 to 10 mm or no screen. In the present invention, particularly preferred is grinding with no screen or additional grinding using a screen with a mesh size of 10 mm in the grinding step.

In this grinding step, coarse grinding may be performed before grinding the freeze-dried material. This coarse grinding allows more efficient grinding. The coarse grinding may be performed by any method, such as manual grinding using a slice, spatula, morta, or the like. The coarse grinding conditions are not limited to particular conditions, but the freeze-dried material is preferably coarse-ground under the conditions that provide a coarse-ground material having the longest side of about 3 to 5 cm.

(Other Steps)

The polysaccharide powder having a desired particle size distribution according to the present invention is obtained by the polysaccharide solution preparation step, the freeze-drying step, and the grinding step. After the powdering step, a sieving step (size classification step) may be performed as desired. This sieving step can remove excessively large powder. The opening of a sieve when this step is performed is not limited to particular sizes, but preferably 710 to 1000 µm to remove excessively large powder. The sieving step (size classification step) may be performed under vibrations as desired. The sieving under vibrations can increase the amount of the powder recovered. The vibration conditions in the sieving under vibrations are not limited to particular conditions, but the vibration is preferably performed, for example, at an amplitude of 1 to 2 mm/g at 20° C. to 30° C. for 3 to 10 minutes.

The above method provides the polysaccharide powder having a desired particle size distribution according to the present invention.

The polysaccharide powder of the present invention can exhibit good water-solubility (rapid dissolution in water) as described above. Therefore, the polysaccharide powder of the present invention is preferred as an anti-adhesive material and can be quickly used in urgent application in surgical practice. Therefore, the present invention also provides an anti-adhesive material containing the polysaccharide powder of the present invention.

The anti-adhesive material of the present invention may include only the polysaccharide powder of the present invention or may further include another component to form a polysaccharide composition. In the latter case, another component may be in a contact state with the polysaccharide powder to form a polysaccharide composition, or may be in a non-contact state with the polysaccharide powder until mixing at the time of use. Another component are not limited to particular components and appropriately selected according to the type of polysaccharide powder or the like. Specific examples include pH adjusters and polymer materials. The another component may be used alone or in mixture, or at least one pH adjuster and at least one polymer material may be used in combination.

Of the above components, the pH adjuster may be mainly an aqueous solution, a water-containing solvent, a salt (powder), or the like for controlling the pH of the polysaccharide powder/polysaccharide composition according to the present invention in the range of 7.5 to 12. Specific examples of pH adjusters include, but are not limited to, sodium hydrogen carbonate aqueous solution or powder, phosphate buffer (disodium hydrogen phosphate-potassium dihydrogen phosphate) and acetate-ammonia buffer. Of these, sodium hydrogen carbonate can be suitably used as a pH adjuster for medical use from a safety viewpoint since about 7% aqueous solutions (pH 8.3) of sodiumhydrdgen carbonate have been used for intravenous injection. An example form of the above composition is a two-component system of a 1% to 80% (w/v) aqueous solution of the polysaccharide powder and water separated from the aqueous solution and having a pH adjusted to pH 7.5 to 10.5. In this system, the both are mixed at the time of use to form a mixed aqueous solution containing the polysaccharide powder at a final concentration of 0.1% to 60% (w/v). To a 1% to 80% (w/v) aqueous solution of the polysaccharide powder, a salt of the pH adjuster may be added and dissolved with mixing at the time of use to provide a mixed aqueous solution containing the polysaccharide powder at a final concentration of 0.1% to 80% (w/v). The mixing can be performed by a selected ordinary mixing method preferably until a uniform mixed state is obtained such that desired reactions proceed.

The polymer material is not particularly limited, but preferably can, for example, serve to control a hardness of a hydrous gel obtained by crosslinking the polysaccharide composition and properties of the hydrous gel. From this point of view, the polymer material preferably has two or more primary amino groups, thiol groups, or hydroxyl groups per molecule of the polymer material. Specific polymer materials include polyalkylene glycol derivatives, polypeptides, polysaccharides, and derivatives thereof. A content of the polymer material in the polysaccharide composition according to the present invention is preferably, but not necessarily, 5 to 50 wt % with respect to the entire polysaccharide composition.

Examples of the polyalkylene glycol derivatives include polyethylene glycol (PEG) derivatives, polypropylene glycol derivatives, polybutylene glycol derivatives, block copolymer derivatives of polypropylene glycol-polyethylene glycol, and random copolymer derivatives. Examples of base polymer backbones of polyethylene glycol derivatives include ethylene glycol, diglycerol, pentaerythritol, and hexaglycerol. A molecular weight of the polyalkylene glycol derivatives is not particularly limited, but is preferably 100 to 50,000, more preferably 1,000 to 20,000.

Examples of the polyethylene glycol derivatives include, but are not limited to, ethylene glycol-type polyethylene glycol derivatives having thiol groups at both terminals and having a weight-average molecular weight of 1,000, 2,000, 6,000 or 10,000; ethylene glycol-type polyethylene glycol derivatives having amino groups at both terminals and having a weight-average molecular weight of 1,000, 2,000, 6,000 or 10,000; trimethylolethane-type polyethylene glycol derivatives having thiol groups at three terminals and having a weight-average molecular weight of 5,000 or 10,000; trimethylolethane-type polyethylene glycol derivatives having amino groups at three terminals and having a weight-average molecular weight of 5,000 or 10,000; diglycerol-type polyethylene glycol derivatives having thiol groups at four terminals and having a weight-average molecular weight of 5,000, 10,000 or 20,000; diglycerol-type polyethylene glycol derivatives having amino groups at four terminals and having a weight-average molecular weight of 5,000, 10,000 or 20,000; pentaerythritol-type polyethylene glycol derivatives having thiol groups at four terminals and having a weight-average molecular weight of 10,000 or 20,000; pentaerythritol-type polyethylene glycol derivatives having amino groups at four terminals and having a weight-average molecular weight of 10,000 or 20,000; hexaglycerol-type polyethylene glycol derivatives having thiol groups at eight terminals and having a weight-average molecular weight of 10,000 or 20,000; and hexaglycerol-type polyethylene glycol derivatives having amino groups at eight terminals and having a weight-average molecular weight of 10,000 or 20,000. As used herein, the term "weight-average molecular weight" refers to a value expressing an average molecular weight of polymers. Since polymers are mixed molecules having the same basic structural unit and different molecular lengths (chain lengths), polymers have a molecular weight distribution depending on the difference in chain length of molecules. In order to express the molecular weight, an average molecular weight is used. The average molecular weight includes weight-average molecular weight and number-average molecular weight. The weight-average molecular weight is used herein. The value (100%) of the weight-average molecular weight in the present invention encompasses 110% of the value as the upper limit and 90% of the value as the lower limit. Polyethylene glycol derivatives can be prepared in accordance with, for example, the method as described in Chapter 22 of Poly (ethylene Glycol) Chemistry: Biotechnical and Biomedical Applications, edited by J. Milton Harris, Plenum Press, NY (1992). The polyethylene glycol derivatives can be further chemically modified to contain one or more primary amino groups or thiol groups. The polyethylene glycol derivatives are available from NOF Corporation under, for example, SUNBRIGHT HGEO-20TEA and SUNBRIGHT PTE-10TSH.

Examples of the polypeptides include, but are not limited to, collagen, gelatin, albumin, and polylysine. Examples of the polysaccharide include, but are not limited to, pectin, hyaluronic acid, chitin, chitosan, carboxymethyl chitin, carboxymethyl chitosan, chondroitin sulfate, keratin sulfate, keratosulfate, heparin, and derivatives thereof.

In the polysaccharide composition containing the polysaccharide powder and the polymer material, suitable combinations of the polysaccharide powder and the polymer material are as follows. It is noted that the form (e.g., sheet, powder, liquid) of these combinations can be appropriately selected.

(a) Combination of active esterified pectin with at least one polymer material selected from the group consisting of ethylene glycol-type PEG derivatives having thiol groups at two terminals, ethylene glycol-type PEG derivatives having amino groups at two terminals, trimethylolethane-type PEG derivatives having thiol groups at three terminals, trimethylolethane-type PEG derivatives having amino groups at three terminals, pentaerythritol-type PEG derivatives having thiol groups at four terminals, pentaerythritol-type PEG derivatives having amino groups at four terminals, hexaglycerol-type PEG derivatives having thiol groups at eight terminals, hexaglycerol-type PEG derivatives having amino groups at eight terminals, albumin, gelatin, collagen, polylysine, pectin, chitosan, chitin, and carboxymethyl (CM) chitin.

(b) Combination of active esterified CM dextran with at least one polymer material selected from the group consisting of ethylene glycol-type PEG derivatives having thiol groups at two terminals, ethylene glycol-type PEG derivatives having amino groups at two terminals, trimethylolethane-type PEG derivatives having thiol groups at three terminals, trimethylolethane-type PEG derivatives having amino groups at three terminals, pentaerythritol-type PEG derivatives having thiol groups at four terminals, pentaerythritol-type PEG derivatives having amino groups at four terminals, hexaglycerol-type PEG derivatives having thiol groups at eight terminals, hexaglycerol-type PEG derivatives having amino groups at eight terminals, albumin, gelatin, collagen, polylysine, pectin, chitosan, chitin, and CM chitin.

(c) Combination of active esterified CM pullulan with at least one polymer material selected from the group consisting of ethylene glycol-type PEG derivatives having thiol groups at two terminals, ethylene glycol-type PEG derivatives having amino groups at two terminals, trimethylolethane-type PEG derivatives having thiol groups at three terminals, trimethylolethane-type PEG derivatives having amino groups at three terminals, pentaerythritol-type PEG derivatives having thiol groups at four terminals, pentaerythritol-type PEG derivatives having amino groups at four terminals, hexaglycerol-type PEG derivatives having thiol groups at eight terminals, hexaglycerol-type PEG derivatives having amino groups at eight terminals, albumin, gelatin, collagen, polylysine, pectin, chitosan, chitin, and CM chitin.

(d) Combination of active esterified CM hydroxyethyl starch with at least one polymer material selected from the group consisting of ethylene glycol-type PEG derivatives having thiol groups at two terminals, ethylene glycol-type PEG derivatives having amino groups at two terminals, trimethylolethane-type PEG derivatives having thiol groups at three terminals, trimethylolethane-type PEG derivatives having amino groups at three terminals, pentaerythritol-type PEG derivatives having thiol groups at four terminals, pentaerythritol-type PEG derivatives having amino groups at four terminals, hexaglycerol-type PEG derivatives having thiol groups at eight terminals, hexaglycerol-type PEG derivatives having amino groups at eight terminals, albumin, gelatin, collagen, polylysine, pectin, chitosan, chitin, and CM chitin.

(e) Combination of active esterified pectin with at least one polymer material selected from the group consisting of ethylene glycol-type PEG derivatives having thiol groups at both terminals and having a weight-average molecular weight of 1,000, 2,000, 6,000 or 10,000; ethylene glycol-type PEG derivatives having amino groups at both terminals and having a weight-average molecular weight of 1,000, 2,000, 6,000 or 10,000; trimethylolethane-type PEG derivatives having thiol groups at three terminals and having a weight-average molecular weight of 5,000 or 10,000; trimethylolethane-type PEG derivatives having amino groups at three terminals and having a weight-average molecular weight of 5,000 or 10,000; diglycerol-type PEG derivatives having thiol groups at four terminals and having a weight-average molecular weight of 5,000, 10,000 or 20, 000; diglycerol-type PEG derivatives having amino groups at four terminals and having a weight-average molecular weight of 5,000, 10,000 or 20, 000; pentaerythritol-type PEG derivatives having thiol groups at four terminals and having a weight-average molecular weight of 10,000 or 20,000; pentaerythritol-type PEG derivatives having amino groups at four terminals and having a weight-average molecular weight of 10,000 or 20,000; hexaglycerol-type PEG derivatives having thiol groups at eight terminals and having a weight-average molecular weight of 10,000 or 20,000; hexaglycerol-type polyethylene glycol derivatives having amino groups at eight terminals and having a weight-average molecular weight of 1.0,000 or 20,000.

(f) Combination of active esterified CM dextran with at least one polymer material selected from the group consisting of ethylene glycol-type PEG derivatives having thiol groups at both terminals and having a weight-average molecular weight of 1,000, 2,000, 6,000 or 10,000; ethylene glycol type PEG derivatives having amino groups at both terminals and having a weight-average molecular weight of 1,000, 2,000, 6,000 or 10,000; trimethylolethane-type PEG derivatives having thiol groups at three terminals and having a weight-average molecular weight of 5,000 or 10,000; trimethylolethane-type PEG derivatives having amino groups at three terminals and having a weight-average molecular weight of 5,000 or 10,000; diglycerol-type PEG derivatives having thiol groups at four terminals and having a weight-average molecular weight of 5,000, 10,000 or 20, 000; diglycerol-type PEG derivatives having amino groups at four terminals and having a weight-average molecular weight of 5,000, 10,000 or 20, 000; pentaerythritol-type PEG derivatives having thiol groups at four terminals and having a weight-average molecular weight of 10,000 or 20,000; pentaerythritol-type PEG derivatives having amino groups at four terminals and having a weight-average molecular weight of 10,000 or 20,000; hexaglycerol-type PEG derivatives having thiol groups at eight terminals and having a weight-average molecular weight of 10,000 or 20,000; and hexaglycerol-type PEG derivatives having amino groups at eight terminals and having a weight-average molecular weight of 10,000 or 20,000.

(g) Combination of active esterified pullulan with at least one polymer material selected from the group consisting of ethylene glycol-type PEG derivatives having thiol groups at both terminals and having a weight-average molecular weight of 1,000, 2,000, 6,000 or 10,000; ethylene glycol-type PEG derivatives having amino groups at both terminals and having a weight-average molecular weight of 1,000, 2,000, 6,000 or 10,000; trimethylolethane-type PEG derivatives having thiol groups at three terminals and having a weight-average molecular weight of 5,000 or 10,000; trimethylolethane-type PEG derivatives having amino groups at three terminals and having a weight-average molecular weight of 5,000 or 10,000; diglycerol-type PEG derivatives having thiol groups at four terminals and having a weight-average molecular weight of 5,000, 10,000 or 20,000; diglycerol-type PEG derivatives having amino groups at four terminals and having a weight-average molecular weight of 5,000, 10,000 or 20,000; pentaerythritol-type PEG derivatives having thiol groups at four terminals and having a weight-average molecular weight of 10,000 or 20,000; pentaerythritol-type PEG derivatives having amino groups at four terminals and having a weight-average molecular weight of 10,000 or 20,000; hexaglycerol-type PEG derivatives having thiol groups at eight terminals and having a weight-average molecular weight of 10,000 or 20,000; and hexaglycerol-type PEG derivatives having amino groups at eight terminals and having a weight-average molecular weight of 10,000 or 20,000.

(h) Combination of active esterified CM hydroxyethyl starch with at least one polymer material selected from the group consisting of ethylene glycol-type PEG derivatives having thiol groups at both terminals and having a weight-average molecular weight of 1,000, 2,000, 6, 000 or 10, 000; ethylene glycol-type PEG derivatives having amino groups at both terminals and having a weight-average molecular weight of 1,000, 2,000, 6,000 or 10, 000; trimethylolethane-type PEG derivatives having thiol groups at three terminals and having a weight-average molecular weight of 5,000 or 10,000; trimethylolethane-type PEG derivatives having amino groups at three terminals and having a weight-average molecular weight of 5,000 or 10,000; diglycerol-type PEG derivatives having thiol groups at four terminals and having a weight-average molecular weight of 5,000, 10,000 or 20, 000; diglycerol-type PEG derivatives having amino groups at four terminals and having a weight-average molecular weight of 5,000, 10, 000 or 20, 000; pentaerythritol-type PEG derivatives having thiol groups at four terminals and having a weight-average molecular weight of 10,000 or 20,000; pentaerythritol-type PEG derivatives having amino groups at four terminals and having a weight-average molecular weight of 10,000 or 20,000; hexaglycerol-type PEG derivatives having thiol groups at eight terminals and having a weight-average molecular weight of 10,000 or 20,000; and hexaglycerol-type PEG derivatives having amino groups at eight terminals and having a weight-average molecular weight of 10,000 or 20,000.

A mixing ratio of the polysaccharide powder to the polymer material (polysaccharide powder/polymer material) is preferably SD/AP =polysaccharide powder/polymer material (weight ratio). The polymer material of more than 80 wt % would inhibit the self crosslink ability of the polysaccharide powder, whereas the polymer material of less than 2 wt % would make it difficult to control a hardness of hydrous gel finally obtained and its properties.

The anti-adhesive material formed from the polysaccharide composition may be provided in a desired form, such as sheet, powder, and liquid. A powdery polymer material may be added to the polysaccharide powder of the present invention to form a powdery polysaccharide composition. A salt of a pH adjuster in a powder form maybe added to the polysaccharide powder of the present invention or the powdery polysaccharide composition to form a powdery polysaccharide composition containing the salt of the pH adjuster.

The powdery polysaccharide composition or the powdery polysaccharide composition containing a salt of a pH adjuster can be granulated to produce a granulated material. The powdery polysaccharide composition and the powdery polysaccharide composition containing a salt of a pH adjuster can be pressed to form a sheet or plate. A sheet-shaped polysaccharide composition can be obtained by adhesion of a polymer material in a powder form to a heat-dried sheet or freeze-dried sheet of the polysaccharide powder or attachment of a polymer material to such a sheet by a coating process. As used herein, the term "attachment" means the state where the surface of a sheet is covered with a polymer material by impregnation of the surface of the sheet with the polymer material. It also means the state where the surface of a sheet and the inner surface of pores inside the sheet are covered with a polymer material when the sheet has a porous structure.

Alternatively, an aqueous solution of the polysaccharide powder and an aqueous solution of the polymer material may be prepared separately as two-liquid type. Mixing these aqueous solutions can form hydrous gel containing the polysaccharide powder and the polymer material. The concentration of the polysaccharide powder in the aqueous solution is preferably 1% to 80% (w/v), and the concentration of the polymer material in the aqueous solution is preferably 1% to 80% (w/v). In particularly, water for dissolving the polymer material may be water prepared to have pH 7.5 to 10.5. A salt of a pH adjuster may be added at the time of mixing by using pure water or a buffer. The total final concentration of the polysaccharide powder and the polymer material is preferably 0.1% to 80% (w/v) after mixing the aqueous solution of the polysaccharide powder and the aqueous solution of the polymer material.

The sheet-shaped polysaccharide composition can be cross-linked in the presence of water. In this case, the above pH adjuster can be used as water. The pH adjuster is preferably an aqueous solution with pH 7.5 to 10.5. The pH adjuster in a powder form may adhere to the sheet-shaped polysaccharide composition.

The sheet-shaped polysaccharide composition is formed by dissolving the polysaccharide powder in water and processing the solution in a desired form and drying it, followed by an attachment step of attaching the polymer material to the resulting sheet-shaped material of the polysaccharide powder. The attachment step involves impregnating the sheet-shaped material with a solution containing the polymer material and a non-aqueous volatile organic solvent and drying it. This allows attachment of the polymer material without damaging the shape of the surface of the sheet-shaped polysaccharide powder. The "non-aqueous volatile organic solvent" means a volatile organic solvent that is incompatible with water. Examples of the non-aqueous volatile organic solvents include, but are not limited to, chloroform and dichloromethane.

In the present invention, examples of dose forms of the anti-adhesive material include, but are not limited to, liquid, sheet, powder, paste, and aerosol. The polysaccharide powder or polysaccharide composition as an anti-adhesive material can be processed in a desired form as described above prior to use.

The polysaccharide composition containing the polymer material can be used in a mixture with the pH adjuster. In mixing the polysaccharide composition with the pH adjuster, the both may be previously mixed (premixed) or may be properly mixed at the time of use. The addition of an aqueous solution of the pH adjuster or the like at the time of use allows application of the anti-adhesive material to a desired local area.

The polysaccharide composition can further contain widely known additives provided that they do not interfere with the characteristics of the present invention. In this case, it is particularly preferred to use biologically acceptable additives. Examples of the additive include, but are not limited to, curing catalysts, fillers, plasticizers, softeners, stabilizers, dehydrating agents, colorants, anti-sagging agents, thickeners, physical property controlling agents, reinforcing agents, thixotropic agents, anti-degradants, flame retardants, antioxidants, ultraviolet absorbers, pigments, solvents, carriers, excipients, antiseptics, binders, swelling agents, isotonic agents, solubilizing agents, preservatives, buffers, and diluents. These additives may be contained alone or in combination.

Specific examples of the additive include water, physiological saline, pharmaceutically acceptable organic solvents, gelatin, collagen, polyvinyl alcohol, polyvinylpyrrolidone, carboxyvinyl polymer, carboxymethyl cellulose sodium, sodium polyacrylate, sodium alginate, water-soluble dextran, carboxymethyl starch sodium, pectin, methyl cellulose, ethyl cellulose, xanthan gum, gum arabic, tragacanth, casein, agar, diglycerol, propylene glycol, polyethylene glycol, vaseline, paraffin, stearyl alcohol, stearic acid, human serum albumin (HSA), mannitol, sorbitol, lactose, PBS, nonionic surfactants, biodegradable polymers, serum-free media, surfactants acceptable as pharmaceutical additives, and biologically acceptable buffers of physiological pH.

The carriers to be used are selected from the above list properly or in combination depending on the area for application but are not limited thereto. They can be prepared as a pharmaceutical preparation, such as aerosols and pastes, using a suitable propellant.

The anti-adhesive material of the present invention can be provided as a kit containing the above pH adjuster for convenience at the time of use. With regard to the anti-adhesive material, the polysaccharide powder, the polysaccharide composition and/or the pH adjuster can be packed or contained in a package in an unmixed state together with or separately from the anti-adhesive material. The package may contain another component that may be used as an anti-adhesive material. The kit can include the polysaccharide powder or polysaccharide composition in the form of powder, sheet, or aqueous solution which may or may not contain the pH adjuster in the form of aqueous solution or powder.

As used herein, the term "anti-adhesive material" means a material that is used to prevent adhesion in or around the area to be prevented from adhesion in living bodies, wherein the material is composed of biologically less-toxic and safe components and is thus biologically acceptable. The anti-adhesive material may be biodegradable or non-biodegradable, and preferably biodegradable.

The anti-adhesive effect is exerted by applying the anti-adhesive material to a target area and optionally covering adhesion areas or possible adhesion areas with the anti-adhesive material to inhibit the adhesion. The anti-adhesive material is applied to a target area, and the other desired area is bonded thereto and fixed, which is then allowed to stand or pressed for a certain period of time. A fixing tool or the like can be used here.

The present invention provides a method of preventing biological adhesion, wherein the method includes bringing the anti-adhesive material into contact with a desired area in the presence of water. The contact of the anti-adhesive material with a desired area is achieved by spraying a powder anti-adhesive material to the desired area, or filling or coating the desired area with a powder anti-adhesive material. In the case of sheet-like anti-adhesive materials, the contact is achieved by sticking, filling, covering, pressing, or standing. In the case of liquid anti-adhesive materials, the contact is achieved by coating, spraying, dropping, painting or plastering. The biological adhesion prevention can be carried out by these means. Since the polysaccharide powder of the present invention is readily dissolved in water, the polysaccharide powder for use as an anti-adhesive material meets the clinical requirements. The polysaccharide powder of the present invention also can avoid risks of infectious diseases or the like because it has natural or artificial polysaccharide as a main backbone without using tissue-derived biomaterials for safety. The components themselves in the polysaccharide powder of the present invention and their decomposition products are less toxic and the polysaccharide powder of the present invention is designed to exhibit biodegradation and bioabsorption because the polysaccharide forms a main backbone.

Since the polysaccharide powder used in the present invention reduces preparation procedures expected to be carried out in advance before use and can be thus quickly used in urgent application without requiring a special device for using the polysaccharide powder, the polysaccharide powder is easily available to anyone. Since the polysaccharide powder used in the present invention can be provided as polysaccharide powder alone or a polysaccharide composition containing the polysaccharide powder, a wide range of applications are available. The polysaccharide composition does not interfere with the above characteristics of the polysaccharide powder.

The polysaccharide powder and polysaccharide composition of the present invention can be processed into various forms, including powder, sheet, and granule, and can be used properly depending on the purpose. A method of producing the polysaccharide powder and the polysaccharide composition is simple because the method involves only mixing necessary reagents and heating them without requiring special devices or the like. In view of the above characteristics, the polysaccharide powder and the composition thereof according to the present invention are preferred as an anti-adhesive material.

EXAMPLES

The advantageous effects of the present invention will be described below by way of Examples and Comparative Examples. It should be noted that the technical scope of the present invention is not limited only to the following Examples. The expression "part" or "%" may be used in the following Examples, and it indicates "part by weight" or "wt %" unless otherwise specified. Unless otherwise specified, each procedure is carried out at room temperature (25° C.).

Synthesis Example 1

Synthesis of Polysaccharide

In a 500 mL flask, 10 g of dextrin (Sandec SD #100, available from Meito Sangyo Co., Ltd., Mw=15 kDa) was dissolved in 62.5 g of pure water until no aggregation or cloudiness was found, and then 62.5 g of a 36 wt % NaOH aqueous solution was added and stirred at room temperature (25° C.) for 90 minutes. To the mixture, an aqueous solution of chloroacetic acid, which was prepared by addition of distilled water to 10.31 g (109.1 mmol) of chloroacetic acid up to 75 g, was added and reacted at 60° C. for 6 hours. After cooling to room temperature (25° C.), 80 mL of a 20% HCl aqueous solution was added to give a reaction solution containing CM dextrin. Next, to a 5 L beaker containing 4450 mL of ethanol and 180 mL of water, the entire volume of the reaction solution obtained above was poured with stirring. The precipitates were collected by filtration and washed first with 2 L of a 90% aqueous solution of ethanol and next with 2 L of ethanol. They were dried under reduced pressure at room temperature (25° C.) for 24 hours to give CM dextrin. The amount of CM groups in the CM dextrin thus obtained was 0.8 mmol/g. The amount of CM groups was measured according to the following method.

(Method of Measuring Amount of Carboxy Groups in Polysaccharide)

0.2 g (A g) of a polysaccharide (CM dextrin) was weighed out and added to a mixed solution containing 20 mL of a 0.1 mol/L aqueous solution of sodium hydroxide and 10 mL of a 80 vol % aqueous solution of methanol and stirred at 25° C. for 3 hours. To the solution, a 1.0% phenolphthalein/90 vol % ethanol aqueous solution was added dropwise and acid-base back titration was performed using 0.05 mol/L sulfuric acid to measure the volume ($V_1$ (mL)) of 0.05 mol/L sulfuric acid used. The volume ($V_0$ (mL)) of 0.05 mol/L sulfuric acid used in a blank without addition of acidic polysaccharide was measured, and the amount (B mmol/g) of carboxy groups in the polysaccharide was calculated according to Formula (1). The 0.1 mol/L aqueous solution of sodium hydroxide and the 0.05 mol/L sulfuric acid both have a titer of 1.00.

[Equation 1]

$$B=(V_0-V_1)\times 0.1/A \quad \text{Formula (I):}$$

wherein A represents a mass (g) of acidic polysaccharide; and B represents an amount of carboxy groups (mmol/g).

To a 1 L flask, 10 g of the CM dextrin obtained above (8 mmol based on the amount of acid group) and 300 g of DMSO were added and completely dissolved with stirring at room temperature (25° C.). Then, 12 g (104 mmol) of N-hydroxysuccinimide (NHS) (available from Wako Pure Chemical Industries, Ltd.) was added and completely dissolved with stirring at room temperature (25° C.). Next, 20.1 g (104 mmol) of 1-ethyl-3-dimethylaminopropylcarbodiimide hydrochloride (EDC) (available from Wako Pure Chemical Industries, Ltd.) was added and completely dissolved with stirring at room temperature (25° C.), followed by stirring at 23° C. for 16 hours to give a reaction solution 1.

To the reaction solution 1, 20.2 g of citric acid was added and mixed for 20 minutes to give a reaction solution 2.

The entire volume of the reaction solution 2 was added to a 3 L beaker containing 2 L of a mixture of methanol and acetone (1:4 v/v) with stirring. After standing, a supernatant was removed by decantation and 800 mL of a mixuture of methanol and acetone (1:4 v/v) was added. The mixture was filtered under suction through a No. 5A filter paper with ϕ95 mm, Kiriyama Rohto, whereby the precipitates were collected by filtration. The residue on a funnel was washed with 1600 mL of a mixture of methanol and acetone (1:4 v/v).

The residue was dried under reduced pressure at 40° C. for 24 hours to give NHS-linked CM dextrin (NHS introduction rate: 70% to 100%). The NHS-linked CMdextrin thus obtained had a molecular weight of 30,000 to 50,000.

Example 1

1. Solution Preparation Step

To a jacket of a 20 L stainless steel tank, cooling water (set to 1.0° C.) was supplied. To the, tank, 3,250 g of distilled water for injection was introduced and 300 g of trehalose was added thereto as a stabilizer. To this solution, 300 g of the NHS-linked CM dextrin obtained above in Synthesis Example 1 was added and stirred at 5.0° C. to 8.0° C. for about 1 hour to dissolve the NHS-linked CM dextrin in the solution. After dissolution, the solution was filtered using a pump and the filtrate was collected in a 20 L bag.

2. Freeze-drying Step

The filtrate collected in the 20 L bag in the Step 1 was dispensed in a volume of 2.5 L into trays for freeze drying (size: 44 cm×29 cm), and thereafter the filtrate was freeze-dried according to the program described below in Table 1 to give a freeze-dried polysaccharide. The following drying step was performed under reduced pressure of 1.7 to 5.1 Pa. In the following pre-freezing step, the shelf temperature was continuously decreased from 5° C. to −50° C. over 165 minutes, followed by freezing at −50° C. for 480 minutes using a freeze dryer (freeze dryer RL-201BS available from Kyowa Vacuum Engineering Co., Ltd). Next, the shelf temperature was gradually increased from −50° C. to −10° C. over 120 minutes, followed by drying at −10° C. for 3,600 minutes. Next, the shelf temperature was gradually increased from −10° C. to 5° C. over 480 minutes, followed by drying at 5° C. for 4,200 minutes. Next, the shelf temperature was gradually increased from 5° C. to 30° C. over 60 minutes, followed by drying at 30° C. for 600 minutes.

TABLE 1

| No. | STEP | SHELF TEMPERATURE | TIME |
|---|---|---|---|
| 1 | PRE-COOLING | 5° C. | 220 MINUTES |
| 2 | LOADING TEMPERATURE | 5° C. | 2 MINUTES |
| 3 | PRE-FREEZING | 5° C. → −50° C. | 165 MINUTES |
| 4 | | −50° C. | 480 MINUTES |
| 5 | PRIMARY DRYING | −50° C. → −10° C. | 120 MINUTES |
| 6 | | −10° C. | 3600 MINUTES |
| 7 | SECONDARY DRYING | −10° C. → 5° C. | 480 MINUTES |
| 8 | | 5° C. | 4200 MINUTES |
| 9 | TERTIARY DRYING | 5° C. → 30° C. | 60 MINUTES |
| 10 | | 30° C. | 600 MINUTES |

3. Coarse Grinding and Ultra centrifugal Grinding Step

The freeze-dried polysaccharide obtained in the Step 2 was coarsely ground (into a size of about 3 cm×3 cm×3 cm) with a spatula, and ground at 6,000 rpm for 20 minutes using an ultra centrifugal mill (available from Retsch-Inc., trade name: ultra centrifugal mill ZM200) to give a ground polysaccharide. In this case, a screen was not used in the ultra centrifugal mill.

4. Sieving Step

The ground polysaccharide thus obtained was placed in an electromagnetic sieve shaker (available from Retsch Inc., trade name: electromagnetic sieve shaker AS200), and classified with a sieve having a sieve opening of 710 μm at an amplitude of 1.2 mm/g for 3 minutes. The material that had passed through the 710 μm sieve was collected to give a classified polysaccharide (polysaccharide powder (1)).

5. Powder Packing Step and Negative Pressure Capping Step

The classified polysaccharide that had sieved in the Step 4 was packed in a vial (Japan Glass Industry Co., Ltd., white vial 30×50) with a precision of 2.5±0.02 g using a powder packing machine (automatic powder measuring and packing machine TM-F51Z3-L). The vial was half capped with a rubber stopper. The half-capped vial was capped under negative pressure to reach the degree of negative pressure of −700 mmHg or more and −400 mmHg (vial (1)).

Example 2

A classified polysaccharide (polysaccharide powder (2)) was obtained by repeating Steps 1 to 4 in Example 1 except that an ultracentrifugal mill equipped with a screen having a screen size (diameter) of 10 mm (available from Retsch Inc., trade name: ultracentrifugal mill ZM200) was used instead in Example 1.

A vial (2) was obtained by repeating Step 5 in Example 1 except that the classified polysaccharide (polysaccharide powder (2)) was used instead in Example 1.

Example 3

A classified polysaccharide (polysaccharide powder (3)) was obtained by repeating Steps 1 to 4 in Example 1 except that an ultracentrifugal mill equipped with a screen having a screen size (diameter) of 8 mm (available from Retsch Inc., trade name: ultracentrifugal mill ZM200) was used instead in Example 1.

A vial (3) was obtained by repeating Step 5 in Example 1 except that the classified polysaccharide (polysaccharide powder (3)) was used instead in Example 1.

Example 4

A classified polysaccharide (polysaccharide powder (4)) was obtained by repeating Steps 1 to 4 in Example 1 except that an ultracentrifugal mill equipped with a screen having a screen size (diameter) of 6 mm (available from Retsch Inc., trade name: ultracentrifugal mill ZM200) was used instead in Example 1.

A vial (4) was obtained by repeating Step 5 in Example 1 except that the classified polysaccharide (polysaccharide powder (4)) was used instead in Example 1.

Comparative Example 1

A classified polysaccharide for comparison (comparative polysaccharide powder (1)) was obtained by repeating Steps 1 to 4 in Example 1 except that an ultracentrifugal mill equipped with a screen having a screen size (diameter) of 2 mm (available from Retsch Inc., trade name: ultracentrifugal mill ZM200) was used instead and the grinding speed was changed to 12,000 rpm in Example 1.

A comparative vial (1) was obtained by repeating Step 5 in Example 1 except that the comparative classified polysaccharide (comparative polysaccharide powder (1)) was used instead in Example 1.

Comparative Example 2

A classified polysaccharide for comparison (comparative polysaccharide powder (2)) was obtained by repeating Steps 1 to 4 in Example 1 except that an ultracentrifugal mill equipped with a screen having a screen size (diameter) of 6 mm (available from Retsch Inc., trade name: ultracentrifugal mill ZM200) was used instead and the grinding speed was changed to 12,000 rpm in Example 1.

A comparative vial (2) was obtained by repeating Step 5 in Example 1 except that the comparative classified polysaccharide (comparative polysaccharide powder (2)) was used instead in Example 1.

Comparative Example 3

A classified polysaccharide for comparison (comparative polysaccharide powder (3)) was obtained by repeating Steps 1 to 4 in Example 1 except that an ultracentrifugal mill equipped with a screen having a screen size (diameter) of 8 mm (available from Retsch Inc., trade name: ultracentrifugal mill ZM200) was used instead and the grinding speed was changed to 12,000 rpm in Example 1.

A comparative vial (3) was obtained by repeating Step 5 in Example 1 except that the comparative classified polysaccharide (comparative polysaccharide powder (3)) was used instead in Example 1.

Comparative Example 4

A classified polysaccharide for comparison (comparative polysaccharide powder (4)) was obtained by repeating Steps 1 to 4 in Example 1 except that an ultracentrifugal mill equipped with a screen having a screen size (diameter) of 10mm (available from Retsch Inc., trade name: ultracentrifugal mill ZM200) was used instead and the grinding speed was changed to 12,000 rpm in Example 1.

A comparative vial (4) was obtained by repeating Step 5 in Example 1 except that the comparative classified polysaccharide (comparative polysaccharide powder (4)) was used instead in Example 1.

Comparative Example 5

A classified polysaccharide for comparison (comparative polysaccharide powder (5)) was obtained by repeating Steps 1 to 4 in Example 1 except that the grinding speed was changed to 12,000 rpm in Example 1.

A comparative vial (5) was obtained by repeating Step 5 in Example 1 except that the comparative classified polysaccharide (comparative polysaccharide powder (5)) was used instead in Example 1.

Comparative Example 6

After the solution preparation step as in Example 1, the filtrate was placed in a 16 ml vial (Japan Glass Industry Co., Ltd., white vial 30×50). The vial was subjected to Step 2 of freeze-drying and Step 5 of negative pressure capping of Example 1 to give Comparative Example (6) (bulk material).

A content (vol %) of polysaccharide powder having a particle size distribution in which the particle size is 200 to 750 μm, the peak top, the particle size at 10% of cumulative volume (D10), the particle size at 50% of cumulative volume (D50), and the particle size at 90% of cumulative volume (D90) are shown below in Table 2 for the polysaccharide powders (1) to (4) and the comparative polysaccharide powders (1) to (5) obtained in Examples and Comparative Examples. In Table 2, the content (vol %) of polysaccharide powder having a particle size distribution in which the particle size is 200 to 750 μm is expressed as the "amount (vol %) of 200 to 750 μm."

The volume frequency distribution (dynamic image analysis) of the polysaccharide powders (1) to (4) and the comparative polysaccharide powders (1) to (5) obtained above in Examples 1 to 4 and Comparative Examples 1 to 4 are shown in the graph in FIG. 1.

In addition, the solubility was evaluated in accordance with the following method for the vials (1) to (4) and the comparison vials (1) to (6) obtained above in Examples and Comparative Examples. The results are shown below in Table 3.

(Evaluation on Solubility)

First, the polysaccharide dry powder (in the vial) is weighed. Next, distilled water for injection is drawn up into a syringe as dissolving water, and the dissolving water (3.4 to 3.6 ml) is injected from a constant height using a jig. The bottom and wall surface of the vial just after injection of the dissolving water is observed and photographed. The manual shaking of the vial is started, and the soluble state is observed every 30 seconds from 0 second at which the shaking of the vial is (manually) started. The vial is photographed simultaneously with the observation of the soluble state. This procedure is continued for total 150 seconds. When complete dissolution is obtained before 150 seconds, the dissolution time is recorded and the procedure is ended. The vial after injection of the dissolving water is weighed, and the amount of the dissolving water injected is calculated.

TABLE 2

| CONDITIONS | EXAMPLE 1 | EXAMPLE 2 | EXAMPLE 3 | EXAMPLE 4 | COMPARATIVE EXAMPLE 1 | COMPARATIVE EXAMPLE 2 | COMPARATIVE EXAMPLE 3 | COMPARATIVE EXAMPLE 4 | COMPARATIVE EXAMPLE 5 |
|---|---|---|---|---|---|---|---|---|---|
| SPIN SPEED (rpm) | 6000 | | | | 12000 | | | | |
| SCREEN SIZE (mm) | — | 10 | 8 | 6 | 2 | 6 | 8 | 10 | — |
| AMOUNT (VOL %) OF 200 TO 750 μm | 64.01 | 55.12 | 30.81 | 37.20 | 10.43 | 19.20 | 17.50 | 21.52 | 18.33 |
| PEAK TOP | 310.02 | 310.02 | 128.15 | 159.82 | 128.15 | 159.82 | 199.32 | 159.82 | 159.82 |
| D10 (μm) | 104.27 | 96.24 | 65.38 | 78.58 | 40.2 | 70.14 | 62.61 | 74.29 | 70.55 |
| D50 (μm) | 246.32 | 219.57 | 139.52 | 164.84 | 96.54 | 129.52 | 133.73 | 141.77 | 132.26 |
| D90 (μm) | 511.13 | 419.68 | 367.64 | 324.20 | 202.95 | 239.45 | 234.8 | 255.41 | 263.86 |

TABLE 3

| CONDITIONS | EXAMPLE 1 | EXAMPLE 2 | EXAMPLE 3 | EXAMPLE 4 | COMPARATIVE EXAMPLE 1 | COMPARATIVE EXAMPLE 2 | COMPARATIVE EXAMPLE 3 | COMPARATIVE EXAMPLE 4 | COMPARATIVE EXAMPLE 5 | COMPARATIVE EXAMPLE 6 (BULK MATERIAL) |
|---|---|---|---|---|---|---|---|---|---|---|
| SPIN SPEED (rpm) | 6000 | | | | 12000 | | | | | — |
| SCREEN SIZE (mm) | — | 10 | 8 | 6 | 2 | 6 | 8 | 10 | — | — |
| 30 SECONDS OR LESS | 15 | 15 | 16 | 16 | 0 | 1 | 2 | 5 | 8 | 0 |
| MORE THAN 30 SECONDS AND 60 SECONDS OR LESS | 1 | 3 | 4 | 2 | 2 | 4 | 5 | 6 | 5 | 0 |
| MORE THAN 60 SECONDS AND 120 SECONDS OR LESS | 0 | 2 | 0 | 1 | 10 | 10 | 11 | 7 | 4 | 0 |
| 120 SECONDS OR MORE | 0 | 0 | 0 | 1 | 8 | 4 | 2 | 2 | 3 | 5 |

Tables 2 and 3 indicate that the polysaccharide powders of the present invention can be significantly readily dissolved in water as compared with the polysaccharide powders of Comparative Examples. Therefore, the anti-adhesive material containing the polysaccharide powders of the present invention is likely to be dissolved within 1 minute at the shortest and expected to be quickly used in urgent application in surgical practices and in various medical practices such as preparation of injections and infusion solutions.

This application is based on Japanese patent application No. 2013-034208 filed on Feb. 25, 2013, which disclosure is entirely incorporated herein by reference.

The invention claimed is:

1. A polysaccharide-containing powder having a particle size distribution in which 30 vol % or more and 70 vol % or less of the total volume of the powder has a particle size of 200 to 750 μm, and a particle size at 10% of cumulative volume (D10) is 65 to 120 μm, and the polysaccharide is at least one member selected from the group consisting of dextrins and dextrans optionally substituted with a carboxyl group, an active ester group, a carboxylate salt, an amino group, and/or an aldehyde group; and wherein the polysaccharide has a molecular weight of 30,000 to 120,000 g/mol.

2. The powder according to claim 1, wherein the particle size at 90% of cumulative volume (D90) is 300 to 520 μm.

3. The powder according to claim 1, having a peak top of 100 to 500 μm.

4. An anti-adhesive material, comprising the powder set forth in claim 1.

5. The powder according to claim 1, wherein the particle size distribution is such that 40 vol % or more and 65 vol % or less of the total volume of the powder has a particle size of 200 to 750 μm.

6. The powder according to claim 1, wherein the particle size at 10% of cumulative volume (D10) is 65 to 110 μm.

7. The powder according to claim 1, wherein the particle size at 90% of cumulative volume (D90) is 320 to 515 μm.

8. The powder according to claim 1, further comprising a component other than the polysaccharide.

9. The powder according to claim 8, wherein the component other than the polysaccharide is oligosaccharide.

10. The powder according to claim 9, wherein the oligosaccharide has a molecular weight of less than 1,000 g/mol.

* * * * *